United States Patent
Lippert et al.

(10) Patent No.: US 9,927,447 B2
(45) Date of Patent: Mar. 27, 2018

(54) COMPOSITION, DEVICE AND IMAGING SYSTEM FOR ANALYSIS USING CHEMILUMINESCENT PROBES

(71) Applicant: Southern Methodist University, Dallas, TX (US)

(72) Inventors: Alexander R. Lippert, Dallas, TX (US); Katherine M. Krenek, Plano, TX (US)

(73) Assignee: SOUTHERN METHODIST UNIVERISITY, Dallas, TX (US)

(*) Notice: Subject to any disclaimer, the term of this patent is extended or adjusted under 35 U.S.C. 154(b) by 0 days.

(21) Appl. No.: 14/741,141

(22) Filed: Jun. 16, 2015

(65) Prior Publication Data
US 2015/0362512 A1    Dec. 17, 2015

Related U.S. Application Data

(60) Provisional application No. 62/012,651, filed on Jun. 16, 2014.

(51) Int. Cl.
| | |
|---|---|
| *G01N 21/76* | (2006.01) |
| *G01N 33/84* | (2006.01) |
| G01N 21/75 | (2006.01) |
| G06K 9/00 | (2006.01) |

(52) U.S. Cl.
CPC ............. *G01N 33/84* (2013.01); *G01N 21/76* (2013.01); *Y10T 436/173076* (2015.01); *Y10T 436/184* (2015.01); *Y10T 436/206664* (2015.01)

(58) Field of Classification Search
CPC ........ G01N 33/84; G01N 33/50; G01N 21/76; G01N 21/75; G01N 21/00; G06K 9/00134; G06K 9/00127; G06K 9/00

USPC .............. 436/110, 106, 121, 135, 164, 165; 422/527, 500
See application file for complete search history.

(56) References Cited

U.S. PATENT DOCUMENTS

| | | |
|---|---|---|
| 3,425,949 A | 2/1969 | Rauhut et al. |
| 8,137,990 B2 | 3/2012 | Akhavan-Tafti et al. |
| 8,389,298 B2 | 3/2013 | Akhavan-Tafti et al. |

(Continued)

OTHER PUBLICATIONS

Shen, Portable Multiplexed Optical Detection for Point of Care, University of Cincinnati, May 11, 2012, pp. 1-82.*

(Continued)

*Primary Examiner* — Christine T Mui
(74) *Attorney, Agent, or Firm* — Edwin S. Flores; Daniel J. Chalker; Chalker Flores, LLP

(57) ABSTRACT

The present invention provides a method for the rapid monitoring of biological analytes in a point-of-care setting by providing a smart phone; providing a sample chamber; providing a sample; providing a dark box with a smartphone holder attached to the dark box top with the camera opening positioned about the aperture, adding a biological specimen suspected of containing a biological analyte in the sample chamber; adding a bis(2,4,6-trichlorophenyl) oxalate, an imidazole and a fluorophore to the sample chamber to react with the biological analyte; placing the sample chamber into the dark box; generating an emission from the fluorophore in response to the reaction with the biological analyte; and recording a set of time-lapse images of the emission with the smartphone.

8 Claims, 3 Drawing Sheets

(56) References Cited

U.S. PATENT DOCUMENTS

| | | | | |
|---|---|---|---|---|
| 2009/0269765 A1* | 10/2009 | Anslyn | ............... | G01N 33/542 |
| | | | | 435/6.11 |
| 2011/0249109 A1* | 10/2011 | Fine | .................. | G01N 21/6408 |
| | | | | 348/79 |
| 2012/0237957 A1* | 9/2012 | Lee | ......................... | C12Q 1/28 |
| | | | | 435/7.92 |
| 2013/0273643 A1* | 10/2013 | Vickers | ............. | G01N 33/6893 |
| | | | | 435/287.2 |
| 2014/0057255 A1* | 2/2014 | Holmes | ................ | G06F 19/366 |
| | | | | 435/6.11 |
| 2014/0072189 A1* | 3/2014 | Jena | .................. | G01N 21/8483 |
| | | | | 382/128 |

OTHER PUBLICATIONS

Khajvand et al, A Study of Chemiluminescence from Reaction of Bis(2,4,6-trichlorophenyl)oxalate-H2O2 in the Presence of a Novel Blue Fluorescer, Furandicarboxylate Derivative, Caspian J. Chem. 2(2013) 9-18.*

The World Press, The Science of Glow Sticks | Light all of the forms of light work the same way: outside energy excites atoms which then release particles of light called photons, 2013, pp. 1-3.*

Yu et al, Fluorescent probes for hydrogen sulfide detection and bioimaging, Chem. Commun., Jun. 6, 2014; 50, 12234-12249.*

Roda, Aldo et al, Integrating Bioluminescence Detection on Smartphones: Mobile Chemistry Platform for Point-of-Need Analysis, Anal. Chem, 2014, 86, 7299-7304. (Year: 2014).*

* cited by examiner

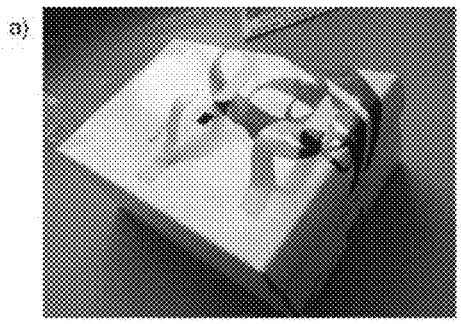
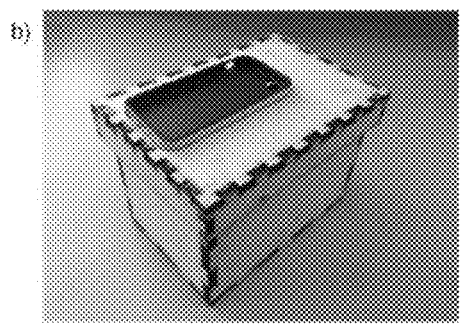
FIGURE 1a-    FIGURE 1b
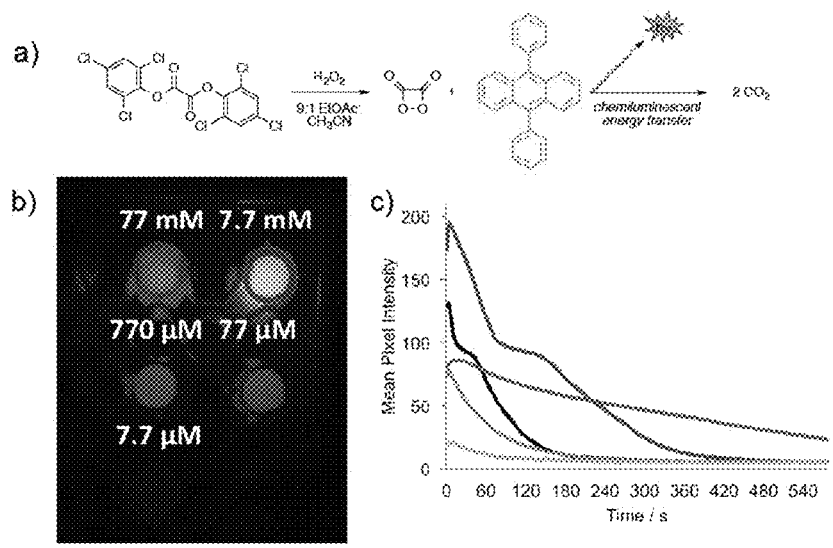
FIGURE 2a-c

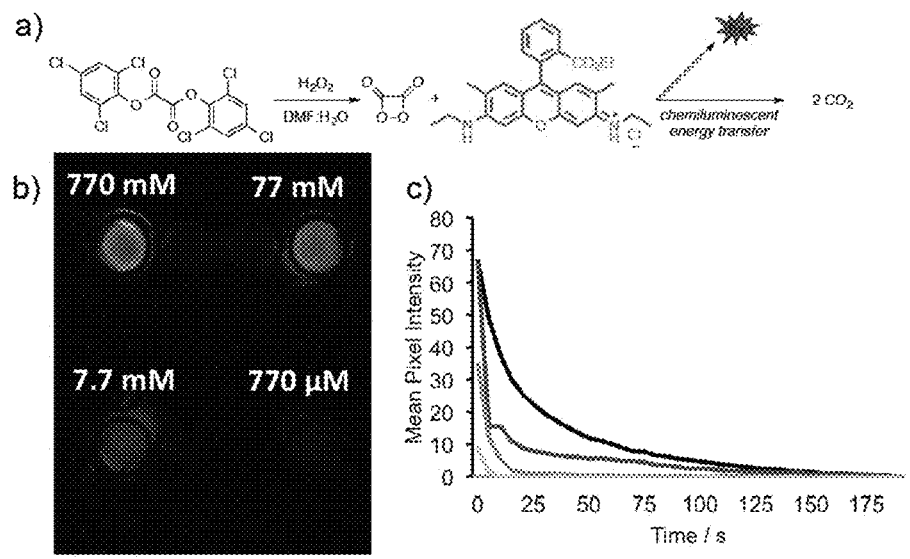
FIGURE 3a-c
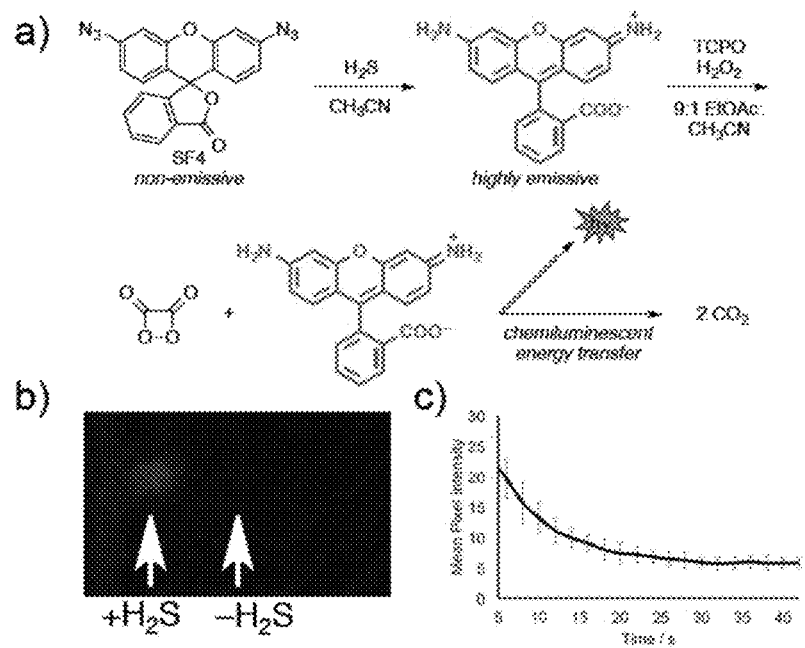
FIGURE 4a-c

COMPOSITION, DEVICE AND IMAGING SYSTEM FOR ANALYSIS USING CHEMILUMINESCENT PROBES

CROSS-REFERENCE TO RELATED APPLICATIONS

This application claims priority based on U.S. Provisional Application No. 62/012,651, filed Jun. 16, 2014. The contents of which is incorporated by reference in its entirety.

TECHNICAL FIELD OF THE INVENTION

The present invention relates in general to the field of biomarker analysis, specifically to systems, kits and devices for rapid monitoring of biological analytes in a point-of-care setting using a smart phone.

STATEMENT OF FEDERALLY FUNDED RESEARCH

None.

INCORPORATION-BY-REFERENCE OF MATERIALS FILED ON COMPACT DISC

None.

BACKGROUND OF THE INVENTION

Chemiluminescent detection of analytes has assumed increasing importance in a number of fields, including biomedical analysis, food testing, pathogen identification, forensic investigations and environmental contaminant screening. For example, spiroadamantane-1,2-dioxetane scaffolds have been extensively used in clinical assays for enzyme activity, and recently have been demonstrated to have efficacy for in vivo imaging, but require highly sensitive and expensive luminometers. Commercially available chemiluminescent probes generally detect enzyme activity, and there is a lack of methods for the detection of $H_2O_2$, $H_2S$, and other reactive small molecule biomarkers.

U.S. Pat. No. 3,425,949 discloses novel chemiluminescent reaction between oxalyl chloride, a peroxide, and water or a suitable alcohol in the presence of a fluorescent compound, and includes a process of admixing reactants including (1) a reactant selected from the group consisting of a ketodiacid halide and an oxalyl halide, (2) sufficient diluent to form a solution of reactants, (3) a peroxide selected from the group consisting of an organohydroperoxide and an organoperacid, and (4) a fluorescer to produce chemiluminescent light and to compositions comprising the reactants.

U.S. Pat. No. 8,137,990 discloses compositions for chemiluminescent detection of hydrogen peroxide and include methods and compound useful for detecting a source of hydrogen peroxide are disclosed wherein a signaling compound of the formula:

is reacted with peroxide. Sig is a non-polymeric organic group, B is a boron atom, and each R is independently selected from hydrogen, alkyl and aryl groups and can be joined together as a straight or branched alkylene chain forming a ring or as an aromatic ring. A detectable product compound of the formula Sig-OH or Sig-O— is produced and detected by measuring color, absorbance, fluorescence, chemiluminescence, or bioluminescence. The signaling compound itself does not possess the detectable property or does so only to a very weak degree. The methods can be used as a detectable signal in assays for peroxide or peroxide-producing enzymes and in assays employing enzyme-labeled specific binding pairs.

U.S. Pat. No. 8,389,298 discloses methods using novel chemiluminescent labels including methods using chemiluminescent label compounds and chemiluminescent labeled conjugates. The compounds comprise an acridan ring bearing an exocyclic ketene dithioacetal group and further contain a labeling substituent which permits attachment to compounds of interest. The novel chemiluminescent compounds and labeled conjugates are convenient to prepare, are highly stable, and generate chemiluminescence rapidly on demand. The compounds and conjugates are useful in assays of an analyte in a sample and in assays employing labeled specific binding pairs. The entire contents of which are incorporated herein by reference.

BRIEF SUMMARY OF THE INVENTION

The present invention provides a smartphone-based platform for chemiluminescence imaging that provides an effective and inexpensive solution to rapid monitoring of biological analytes in point-of-care settings that can include patient self-monitoring at home or medicine in developing countries with limited resources. The high sensitivity of this technique has found utility under a number of applications, but home use and point-of-care chemiluminescent diagnostics are hindered by the need for expensive photon detection equipment.

The present invention includes an attachment that is compatible with commercial smartphones equipped with cameras and includes a novel chemiluminescent reagent system that enables the imaging of arrays of analytes for instant readout of test results of sampled biological fluids, which include urine, saliva, semen, and blood.

The present invention provides a dark box using a smartphone for chemiluminescence imaging comprising a dark box comprising a bottom connected to 4 walls, a removable dark box top position on the 4 walls to form the dark box, and an aperture in the dark box top; and a smartphone holder attached to the dark box top with the camera opening positioned about the aperture, wherein the top may be removed to access a sample. The smartphone holder is adapted to fit a tablet, a mini tablet, a smart phone, a camera phone, or a combination thereof and/or adapted to fit a SAMSUNG® PHONE; LG® PHONE; MICROSOFT® PHONE, MOTOROLA® PHONE, SONY® PHONE, or APPLE® IPHONE®.

The present invention provides a dark box using a smartphone for chemiluminescence imaging comprising a dark box comprising 4 walls to form an open cube, a dark box top connected on the 4 walls to form the dark box, and an aperture in the dark box top; and a smartphone holder attached to the dark box top with the camera opening positioned about the aperture, wherein the dark box may be removed to access a sample inside. The device may further comprise a base adapted to receive the 4 walls. The smartphone holder is adapted to fit a tablet, a mini tablet, a smart phone, a camera phone, or a combination thereof and/or adapted to fit a SAMSUNG® PHONE; LG® PHONE;

MICROSOFT® PHONE, MOTOROLA® PHONE, SONY® PHONE, or APPLE® IPHONE®.

The present invention provides a dark box using a smartphone for chemiluminescence imaging comprising a dark box comprising a bottom connected to 3 fixed walls and 1 movable wall to form an open cube, a dark box top position on the 3 fixed walls and 1 movable wall to form the dark box, and an aperture in the dark box top; and a smartphone holder attached to the dark box top with the camera opening positioned about the aperture, wherein the 1 movable wall may be moved to access a sample inside. The smartphone holder is adapted to fit a tablet, a mini tablet, a smart phone, a camera phone, or a combination thereof and/or adapted to fit a SAMSUNG PHONE; LG PHONE; MICROSOFT® PHONE, MOTOROLA® PHONE, SONY® PHONE, or APPLE® IPHONE®.

The present invention provides a method for the rapid monitoring of biological analytes in a point-of-care setting by providing a smart phone; providing a sample chamber; providing a sample; providing a dark box comprising a bottom connected to 4 walls to form an open cube, a removable dark box top position on the 4 walls to form the dark box, and an aperture in the dark box top; and a smartphone holder attached to the dark box top with the camera opening positioned about the aperture, wherein the top may be removed to access the sample chamber; positioning the smartphone in the smartphone holder to align the camera with the aperture; adding a biological specimen suspected of containing a biological analyte in the sample chamber; adding a bis(2,4,6-trichlorophenyl) oxalate, an imidazole and a fluorophore to the sample chamber to react with the biological analyte; placing the sample chamber into the dark box; generating an emission from the fluorophore in response to the reaction with the biological analyte; and recording a set of time-lapse images of the emission with the smartphone.

The sample may be saliva, exhaled breath condensates, urine, semen, and blood. The method may further include the step of quantifying a pixel intensity from the set of time-lapse images. The biomarker may be Hydrogen sulfide ($H_2S$), hydrogen peroxide ($H_2O_2$), peroxynitrite (ONOO—). The biomarker may be $H_2O_2$ and the fluorophore may be 9,10-diphenylanthracene; the biomarker may be $H_2O_2$ and the fluorophore may be Rhodamine 6G; or the biomarker may be $H_2S$ and the fluorophore may be Rhodamine 110.

The present invention provides a chemiluminescence imaging system for analyzing biomarkers at a point-of-care setting using a smartphone comprising: a dark box comprising a bottom connected to 4 walls to form an open cube, a removable dark box top position on the 4 walls to form the dark box, and an aperture in the dark box top; and a smartphone holder attached to the dark box top with the camera opening positioned about the aperture, wherein the top may be removed to access a sample; and a chemiluminescence reagent system comprising a bis(2,4,6-trichlorophenyl) oxalate, an imidazole and a fluorophore to react with a biomarkers to generate an emission from the fluorophore, wherein a smartphone positioned in the smartphone holder captures a set of time-lapse images of the emission from the fluorophore.

The system may further include a device to quantify a pixel intensity from the set of time-lapse images. The device may be a smart phone, tablet, or computer. The sample may be saliva, exhaled breath condensates, urine, semen, and blood. The biomarker may be Hydrogen sulfide (H2S), hydrogen peroxide (H2O2), peroxynitrite (ONOO—). The biomarker may be H2O2 and the fluorophore may be 9,10-diphenylanthracene; the biomarker may be H2O2 and the fluorophore may be Rhodamine 6G; or the biomarker may be H2S and the fluorophore may be Rhodamine 110. The smartphone holder may be adapted to fit a SAMSUNG® PHONE; LG® PHONE; MICROSOFT® PHONE, MOTOROLA® PHONE, SONY® PHONE, or APPLE® IPHONE®.

The present invention provides a method of analyzing a $H_2O_2$ in an organic solvent in a point-of-care settings by adding a biological specimen suspected of containing $H_2O_2$ in an organic solvent to a reaction chamber; adding bis(2,4,6-trichlorophenyl) oxalate and imidazole to the reaction chamber; forming 1,2-dioxetane-3,4-dione in the reaction chamber; reacting the 1,2-dioxetane-3,4-dione with 9,10-diphenylanthracene detecting a chemiluminescent emission from the 9,10-diphenylanthracene; and recording the chemiluminescent emission. The recording may be a set of time-lapse images. The method may further include quantifying the chemiluminescent emission. The method may further include quantifying a pixel intensity from a set of time-lapse images from the recording. The sample may be saliva, exhaled breath condensates, urine, semen, and blood.

The present invention provides a method of analyzing a $H_2O_2$ in an aqueous solvent by adding a biological specimen suspected of containing $H_2O_2$ in an aqueous solvent to a reaction chamber; adding bis(2,4,6-trichlorophenyl) oxalate and imidazole to the reaction chamber; forming 1,2-dioxetane-3,4-dione in the reaction chamber; reacting the 1,2-dioxetane-3,4-dione with Rhodamine 6G in the reaction chamber; detecting a chemiluminescent emission from the Rhodamine 6G; and recording the chemiluminescent emission. The recording may be a set of time-lapse images. The method may further include quantifying the chemiluminescent emission. The method may further include quantifying a pixel intensity from a set of time-lapse images from the recording. The sample may be saliva, exhaled breath condensates, urine, semen, and blood.

The present invention provides a method of analyzing a $H_2S$ in a biological specimen by adding a biological specimen suspected of containing $H_2S$ to a reaction chamber; adding SF4 to the a reaction chamber; converting the SF4 to Rhodamine 110; adding bis(2,4,6-trichlorophenyl) oxalate and imidazole to the reaction chamber; forming 1,2-dioxetane-3,4-dione in the reaction chamber; detecting a chemiluminescent emission from the Rhodamine 110; and recording the chemiluminescent emission. The recording may be a set of time-lapse images. The method may further include quantifying the chemiluminescent emission. The method may further include quantifying a pixel intensity from a set of time-lapse images from the recording. The sample may be saliva, exhaled breath condensates, urine, semen, and blood.

BRIEF DESCRIPTION OF THE SEVERAL VIEWS OF THE DRAWINGS

For a more complete understanding of the features and advantages of the present invention, reference is now made to the detailed description of the invention along with the accompanying figures and in which:

FIGS. 1a-1b are images of designs for a point-of-care diagnostic platform for biomarker detection.

FIGS. 2a-2c are images of the point-of-care imaging system. FIG. 2a is an image of the reaction scheme for the detection of $H_2O_2$ using TCPO, imidazole, and 9,10-diphenylanthracene. FIG. 2b is an image of 7.7 µM, 77 µM, 770 µM, 7.7 mM, and 77 mM $H_2O_2$. FIG. 2c is a graph quantification of pixel intensity of images in (b).

FIGS. 3a-3c are images of the point-of-care imaging of $H_2O_2$ in an aqueous environment. FIG. 3a is an image Reaction scheme for the detection of $H_2O_2$ using TCPO, imidazole, and a water-soluble dye Rhodamine 6G. FIG. 3b is an image of 7.7 mM, 77 mM, and 770 mM $H_2O_2$. Time-lapse images were acquired in a dark-box using an iPhone 4s with the free application "O!Snap". FIG. 3c is a graph quantification of pixel intensity of images in (b).

FIGS. 4a-4c are images of the point-of-care imaging of $H_2S$. FIG. 4a is an image of the scheme for the chemiluminescenct detection of $H_2S$. FIG. 4b is an image of the chemiluminescence spectra of 500 μM SF4 and 0, 15, 150, and 1500 μM $H_2S$ in $CH_3CN$ for 30 min; then 80 mM $H_2O_2$, 3 mM TCPO, and 3 mM imidazole. FIG. 4c is a graph of the Time-course of the conditions in b) at 1500 μM $H_2S$. FIG. 4b is an image of 500 μM SF4 and 0, 15, 150, and 1500 μM $H_2S$ in $CH_3CN$ for 30 min; then 80 mM $H_2O_2$, 3 mM TCPO, and 3 mM imidazole. Time-lapse images were acquired in a home built dark-box using an iPhone 4s with the free application "O!Snap". FIG. 4c is a graph quantification of pixel intensity of images in FIG. 4b.

DETAILED DESCRIPTION OF THE INVENTION

Figures 5A, 5B, 5C, 5D, 5E:
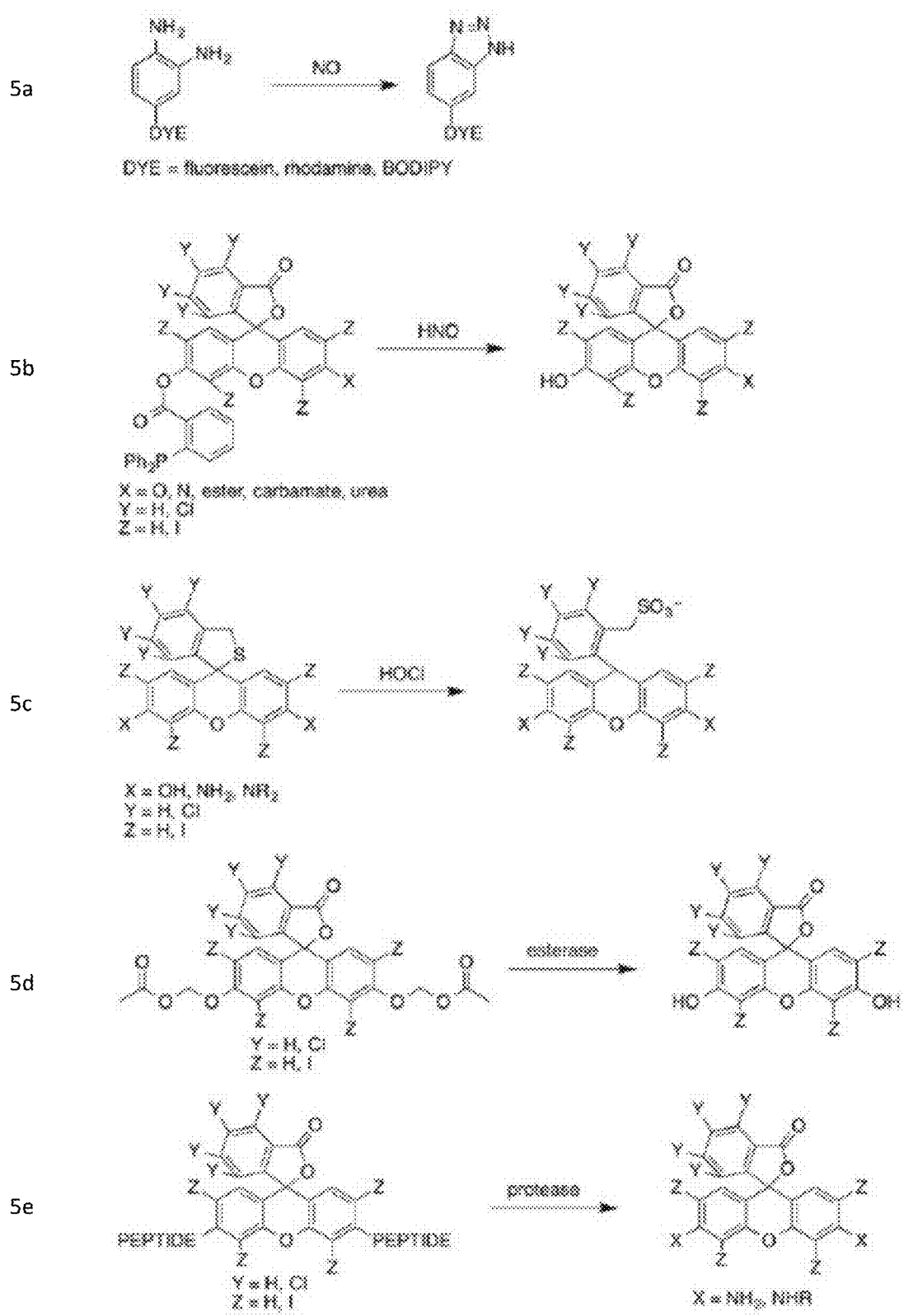
FIG. 5a-5e illustrates the reaction used in the detection of NO (FIG. 5a), HNO (FIG. 5b), HOCl (FIG. 5c), esterases (FIG. 5d), and proteases (FIG. 5e).

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

Hydrogen sulfide ($H_2S$), hydrogen peroxide ($H_2O_2$), peroxynitrite (ONOO—), and other reactive species are endogenous signaling molecules that play important roles in almost every physiological process. Their small size allow these signaling molecules to rapidly diffuse through cellular membranes and mediate many aspects of human health including blood pressure regulation, neurotransmission, and the immune response. Despite their importance, our understanding of the biological chemistry of these reactive signaling molecules is still in its infancy, and much remains to be learned about how the misregulation of reactive species signaling contributes to diseases such as asthma, hypertension, neurodegeneration, and cancer. A key obstacle to understanding and applying these molecules as clinical biomarkers is the lack of methods for their selective and high throughput detection in biological samples. In order to address this key technological challenge and better understand the roles these species play in the course of human pathology, our lab has pioneered innovative reagents that enable the sensitive detection of these species using fluorescence spectrometry, magnetic resonance spectroscopy, and even inexpensive iPhone cameras that show great promise for high-throughput research and point-of-care diagnostics.

Commercially available chemiluminescent probes generally detect enzyme activity, and there is a lack of methods for the detection of $H_2O_2$, $H_2S$, and other reactive small molecule biomarkers. The only reported chemiluminescence probe for $H_2S$, requires incubation with horseradish peroxidase to produce light, which suffers from the key drawback of needing hydrogen peroxide and horseradish peroxidase to produce light, which ultimately precludes in vivo or clinical imaging and complicates in vitro assays. The present invention uses smartphone technology for multiplexed analyte detection at a much lower cost without the need of lenses or optical filters and allows a straightforward quantification of pixel intensity.

The present invention provides a point-of-care imaging system for the visualization of reactive analytes using chemiluminescent probes The present invention provides a smartphone-based platform for chemiluminescence imaging provides an effective and inexpensive solution to rapid monitoring of biological analytes in point-of-care settings that can include patient self-monitoring at home or medicine in developing countries with limited resources. Chemiluminescence consists of light production directly from a chemical bond and is the phenomena responsible for light production in glow sticks and fireflies. The high sensitivity of this technique has found utility under a number of applications, but home use and point-of-care chemiluminescent diagnostics are hindered by the need for expensive photon detection equipment.

The present invention provides an accessory that is compatible with widely available commercial smartphones equipped with CMOS cameras, and a novel chemiluminescent reagent system that enables the imaging of arrays of analytes for instant readout of test results of sampled biological fluids such as urine, saliva, semen, and blood. The present invention provides a designed dark-box, certain reactive analytes such as $H_2O_2$ could be detected and quantified by using inexpensive cameras that are now an integral part of cellular phones.

FIGS. 1a and 1b are images of designs for a point-of-care diagnostic platform for biomarker detection. FIG. 1a is an image of one embodiment of a design consisting of a shoe box with a precisely cut hole and placement where a cellular phone can be taped. FIG. 1b is an image of one embodiment of a design with a wooden dark-box laser cut. A smart phone case is glued to the lid to provide an easy interface for smartphone imaging of analytes. A simple design of the present invention includes a box with an aperture in a portion of the box that is adapted to fit a smartphone camera. FIG. 1b is another embodiment of the present invention that includes a light-tight second generation dark box designed with a laser cut aperture and interlocking areas. In one embodiment, the phone case having a camera cutout is aligned with the laser cut aperture. For example, the laser cut aperture is fitted with an iPhone case attached to the darkbox lid.

As an indicator a novel chemiluminescent reagent system was used to enables the imaging of analytes and allow an instant readout of test results of sampled biological fluids. For example, one embodiment analyzes $H_2O_2$, a validated biomarker of oxidative stress in a number of disease states. The chemiluminescent reagent system included bis(2,4,6-trichlorophenyl) oxalate (TCPO), imidazole, and a blue emitting dye 9,10-diphenylanthracene in a nonpolar solvent mixture of 9:1 ethyl acetate to acetonitrile. Time-lapse images were acquired using our dark-box system, an iPhone 4s, and the "O!Snap" application. although one example of chemiluminescent reagent system included bis(2,4,6-trichlorophenyl) oxalate (TCPO) other reagents may be used, e.g., Bis(2,4-dinitrophenyl) oxalate (DNPO).

FIG. 2a-2c are images illustrating a point-of-care imaging of $H_2O_2$ in an organic solvent system. FIG. 2a is an image of the reaction scheme for the detection of $H_2O_2$ using TCPO, imidazole, and 9,10-diphenylanthracene. FIG. 2b is an image of 7.7 μM, 77 μM, 770 μM, 7.7 mM, and 77 mM $H_2O_2$. FIG. 2c is a graph quantification of pixel intensity of images in (b) using ImageJ. In addition, the present invention can quantify these images to obtain quantitative information from both the pixel intensity and reaction kinetics provides an advantage over existing point-of-care designs that rely on color changes or fluorescent readouts. Another feature of this system is that it can be adapted to other conditions by judicious choice of the dyes.

FIGS. 3a-3c are images of the point-of-care imaging of $H_2O_2$ in an aqueous environment. FIG. 3a is an image Reaction scheme for the detection of $H_2O_2$ using TCPO, imidazole, and a water-soluble dye Rhodamine 6G. FIG. 3b is an image of 7.7 mM, 77 mM, and 770 mM $H_2O_2$. Time-lapse images were acquired in a dark-box using an iPhone 4s with the free application "O!Snap". FIG. 3c is a graph quantification of pixel intensity of images in FIG. 3b.

We have taken advantage of this aspect to develop a platform that will be compatible with aqueous clinical samples including saliva, exhaled breath condensates, urine, semen, and blood. This was accomplished by using the water-soluble red-orange emitting dye Rhodamine 6G in combination with TCPO and imidazole. This system allowed us to image and quantify $H_2O_2$ under aqueous conditions. A second key innovation of our approach is the discovery that previously developed responsive dyes for the fluorescence detection of $H_2S$ and other validated/emerging biomarkers can be adapted towards chemiluminescence detection by judicious choice of a chemiluminescent reagent system.

FIGS. 4a-4c are images of the Point-of-care imaging of $H_2S$. FIG. 4a is an image of the scheme for the chemiluminescent detection of $H_2S$. FIG. 4b is an image of the chemiluminescence spectra of 500 μM SF4 and 0, 15, 150, and 1500 μM $H_2S$ in $CH_3CN$ for 30 min; then 80 mM $H_2O_2$, 3 mM TCPO, and 3 mM imidazole. FIG. 4c is a graph of the Time-course of the conditions in b) at 1500 μM $H_2S$. FIG. 4b is an image of 500 μM SF4 and 0, 15, 150, and 1500 μM $H_2S$ in $CH_3CN$ for 30 min; then 80 mM $H_2O_2$, 3 mM TCPO, and 3 mM imidazole. Time-lapse images were acquired in a home built dark-box using an iPhone 4s with the free application "O!Snap". FIG. 4c is a graph quantification of pixel intensity of images in (b) using ImageJ.

This procedure proceeds in two steps. First, a biological sample is incubated with a responsive turn-on dye such as the $H_2S$ probe SF4. Over a time course of 30-60 minutes, $H_2S$ in the sample will react with the responsive dye to transform it from a colorless non-emissive compound into the highly green emissive dye rhodamine 110. After this incubation period, chemiluminescent reagents TCPO and $H_2O_2$ are added to form the molecule dioxetanedione in situ. Dioxetanedione then rapidly reacts in a chemiluminescent reaction with the emissive rhodamine dye formed from the reaction of $H_2S$ with SF4. In a remarkable demonstration of the sensitivity of this platform, we have imaged $H_2S$ using a dark box and the standard camera in the iPhone 4s to provide a clear visualization of $H_2S$. Time-lapse images acquired with "O!Snap!" iPhone application can be quantified using the free ImageJ software available from the National Institutes of Health. Importantly, reproducible quantification can be achieved using the inexpensive cameras that are a standard component of most cellular phones. Building off this exciting data, we systematically optimized solvents, activated oxalates, catalysts, and reagent concentrations in order to develop a system that can be used for the detection of $H_2S$ in clinical samples and cell cultures with nanomolar sensitivity. Given the availability of responsive dyes for other analytes, as well as innovative new responsive dyes currently being developed in our lab, this invention has the potential to be adapted for the point-of-care imaging of almost any imaginable biomarker.

One embodiment of the present invention includes a dark box having 4 sides attached to a top wherein the top includes an aperture. The aperture extends through the top to allow access from the outside into the interior of the dark box. Attached to the top is a mounting device for a phone having a camera where the camera is aligned with the aperture to allow imaging of the contents of the dark-box. The mounting device may be configured for any current phone having a camera and maybe a phone case or any other device to maintain the location of the phones camera lens relative to the aperture.

In some embodiments, the dark box may have a detachable top that allows access to the interior space of the dark-box. In other embodiments, one or more sides may be moved to allow access to the interior of the dark-box. In still other embodiments the dark-box may be lifted from a bottom that aligns the dark-box. It will be understood that any mechanism known to the skilled artisan may be used to allow access to the interior of the dark-box.

The present invention includes a fully characterized series of reagents that can detect reactive species in solution, in living cells, and in animals and includes reagents for the detection of hydrogen sulfide (HS), hydrogen peroxide ($H_2O_2$), peroxynitrite (ONOO—), and other reactive species in saliva samples and exhaled breath condensates.

FIG. 5a-5e illustrates the reaction used in the detection of NO (FIG. 5a), HNO (FIG. 5b), HOCl (FIG. 5c), esterases (FIG. 5d), and proteases (FIG. 5e). The present invention includes a fully characterized series of reagents that can detect reactive species in solution, in living cells, and in animals and includes reagents for the detection in saliva samples and exhaled breath condensates. In the reaction s of FIG. 5a-5e the dyes in the reactions may be substituted for SF4 to enable our device to detect these analytes.

This procedure proceeds in two steps. First, a biological sample is incubated with a responsive turn-on dye. Over a time course of 30-60 minutes, the analyte in the sample will react with the responsive dye to transform it from a colorless non-emissive compound into the emissive dye. After this incubation period, chemiluminescent reagents TCPO and $H_2O_2$ are added to form the molecule dioxetanedione in situ. Dioxetanedione then rapidly reacts in a chemiluminescent reaction with the emissive dye formed from the reaction of the analyte with emissive dye. Time-lapse images acquired with "O!Snap!" iPhone application can be quantified using the free ImageJ software available from the National Institutes of Health. Importantly, reproducible quantification can be achieved using the inexpensive cameras that are a standard component of most cellular phones. Building off this exciting data, we systematically optimized solvents, activated oxalates, catalysts, and reagent concentrations in order to develop a system that can be used for the detection of an analyte in clinical samples and cell cultures with nanomolar sensitivity. Given the availability of responsive dyes for other analytes, as well as innovative new responsive dyes currently being developed in our lab, this invention has the potential to be adapted for the point-of-care imaging of almost any imaginable biomarker.

The present invention includes the use of the detection of these agents for delineating if and when elevated or reduced levels correlate with various diseases, particularly diseases that affect oral and respiratory health.

In addition, samples may be taken from the blood by collecting samples from finger stick, heel stick, ear stick, or venipuncture.

Prospective collection of biological specimens by non-invasive means includes hair and nail clippings in a non-disfiguring manner; deciduous teeth at time of exfoliation or if routine patient care indicates need for extraction; permanent teeth if routine patient care indicates need for extraction; excreta and external secretions (including sweat); uncannulated saliva collected either in an unstimulated fashion or stimulated by chewing gum base or wax or by applying a dilute citric solution to the tongue; placenta removed at delivery; amniotic fluid obtained at the time of rupture of the membrane prior to or during labor; supra- and subgingival dental plaque and calculus, provided the collection procedure is not more invasive than routine scaling of the teeth and the process is accomplished in accordance with accepted prophylactic techniques; mucosal and skin cells collected by buccal scraping or swab, skin swab, or mouth washings; sputum collected after saline mist nebulization.

The present invention in general will benefit society by the development of low cost point-of-care diagnostics of non-invasive clinical samples. Health care costs are continually increasing due, in part, to increases in the use of expensive instrumentation for lab tests and diagnosis. The present invention provides important data to correlate multi-analyte detection platforms with the presence and aggressiveness of disease.

Examples of other useful dyes include rhodamine, ethidium, dansyl, anthracene, anthracene derivatives (e.g., 1-chloro-9,10-bis(phenylethynyl)-anthracene, 9,10-bis(phenylethynyl)-anthracene), naphthalene, phenanthrene, pyrene, tetracene, pentacene, coronene, chrysene, fluorescein, perylene, rubrene and derivatives thereof. Further, they include phthaloperylene, naphthaloperylene, perynone, phthaloperynone, naphthaloperynone, diphenylbutadiene, tetraphenylbutadiene, coumarin, oxadiazole, aldazine, bis-benzoxazoline, bisstyryl, pyrazine, cyclopentadiene, quinoline metal complexes, aminoquinoline metal complexes, benzoquinoline metal complexes, imine, diphenylethylene, vinylanthracene, diaminocarbazole, pyran, thiopyran, polymethine, merocyanine, imidazole chelated oxynoid compounds, quinacridone, rubrene, stilbene base derivatives, BODIPYs, Rose Bengal, Eu(fod)3, Eu(TTA)$_3$, and Ru(bpy)$_3{}^{++}$ (wherein bpy=2,2'-dipyridyl, etc.

In one embodiment the chemiluminescent reagent system included bis(2,4,6-trichlorophenyl) oxalate (TCPO); however the skilled artisan will readily understand that other reagents may be used in the current system, e.g., Oxalyl halides, oxalyl chloride.

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AB, BBC, AAABCCCC, CBBAAA, CABABB, and so forth. The skilled artisan will understand that typically there is no limit on the number of items or terms in any combination, unless otherwise apparent from the context.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

What is claimed is:

1. A chemiluminescence imaging system for analyzing biomarkers at a point-of-care setting using a smartphone comprising:

a dark box comprising a bottom connected to 4 walls to form an open cube, a removable dark box top position on the 4 walls to form the dark box, and an aperture in the dark box top; and a smartphone holder attached to the dark box top with a camera opening positioned about the aperture, wherein the dark box top may be removed to access a sample;

a device positioned in the smartphone holder wherein the device captures a set of time-lapse images and quantifies a pixel intensity from the set of time-lapse images; and a chemiluminescence reagent system comprising a bis(2,4,6-trichlorophenyl) oxalate, an imidazole and a fluorophore to react with a biomarker in the sample to generate an emission from the fluorophore, wherein the biomarker is Hydrogen sulfide ($H_2S$), hydrogen peroxide ($H_2O_2$), or peroxynitrite (ONOO).

2. The system of claim 1, wherein the device is a smartphone, tablet, or computer.

3. The system of claim 1, wherein the sample is saliva, exhaled breath condensates, urine, semen, or blood.

4. The system of claim 1, wherein the biomarker is $H_2O_2$ and the fluorophore is 9,10-diphenylanthracene; the biomarker is $H_2O_2$ and the fluorophore is Rhodamine 6G; or the biomarker is $H_2S$ and the fluorophore is Rhodamine 110.

5. The system of claim 1, wherein the smartphone holder is adapted to fit a SAMSUNG® PHONE; LG® PHONE; MICROSOFT® PHONE, MOTOROLA® PHONE, SONY® PHONE, or APPLE® IPHONE®.

6. The system of claim 1, wherein the biomarker is $H_2O_2$ and the fluorophore is 9,10-diphenylanthracene.

7. The system of claim 1, wherein the biomarker is $H_2O_2$ and the fluorophore is Rhodamine 6G.

8. The system of claim 1, wherein the biomarker is $H_2S$ and the fluorophore is Rhodamine 110.

* * * * *